(12) United States Patent
Rozzi et al.

(10) Patent No.: US 12,733,840 B2
(45) Date of Patent: Sep. 15, 2026

(54) APPARATUS FOR THE DETECTION OF AT LEAST ONE PARAMETER, IN PARTICULAR KINETIC, IN RELATION TO THE HEART, OR THE MYOCARDIUM, OF A HUMAN BEING OR AN ANIMAL

(71) Applicants: Giacomo Rozzi, Parma (IT); Enrico La Rosa, Parma (IT); Francesco Barresi, Campegine (IT)

(72) Inventors: Giacomo Rozzi, Parma (IT); Enrico La Rosa, Parma (IT); Francesco Barresi, Campegine (IT)

( * ) Notice: Subject to any disclaimer, the term of this patent is extended or adjusted under 35 U.S.C. 154(b) by 573 days.

(21) Appl. No.: 18/027,537

(22) PCT Filed: Sep. 22, 2021

(86) PCT No.: PCT/IB2021/058650

§ 371 (c)(1),
(2) Date: Mar. 21, 2023

(87) PCT Pub. No.: WO2022/064390

PCT Pub. Date: Mar. 31, 2022

(65) Prior Publication Data

US 2023/0371847 A1 Nov. 23, 2023

(30) Foreign Application Priority Data

Sep. 23, 2020 (IT) ........................ 102020000022480

(51) Int. Cl.
*A61B 5/11* (2006.01)

(52) U.S. Cl.
CPC ....... *A61B 5/1107* (2013.01); *A61B 2576/023* (2013.01)

(58) Field of Classification Search
CPC ........................ A61B 5/1107; A61B 2576/023
See application file for complete search history.

(56) References Cited

U.S. PATENT DOCUMENTS

2016/0100095 A1 4/2016 Weingard
2018/0140376 A1 5/2018 Hokka

FOREIGN PATENT DOCUMENTS

JP 2017176307 A 10/2017
JP 2020141896 A 9/2020
WO 2019186768 A1 10/2019

OTHER PUBLICATIONS

Rozzi, Giacomo, et al. "Real-time video kinematic evaluation of the in situ beating right ventricle after pulmonary valve replacement in patients with tetralogy of Fallot: a pilot study." Interactive CardioVascular and Thoracic Surgery 29.4 (2019): 625-631. (Year: 2019).*

(Continued)

*Primary Examiner* — Lindsey G Wehrheim
(74) *Attorney, Agent, or Firm* — SHUTTLEWORTH & INGERSOLL, PLC; Timothy J. Klima

(57) ABSTRACT

An apparatus for detecting at least one parameter, in particular kinetic, in relation to a human/animal heart/myocardium, especially during surgical operations; comprising a detector for detecting spatial or mechanical, movements of said heart/myocardium, and a controller for processing data provided by the detector for providing at least one corresponding parameter, in particular kinetic, in relation to the heart/myocardium. The detector is adapted to detect a distance, or depth, i.e. a variation in distance, or depth, of one or more points of said heart/myocardium, particularly one or more points of a corresponding surface or wall of the heart/myocardium by the detector.

15 Claims, 3 Drawing Sheets

(56) References Cited

OTHER PUBLICATIONS

International Search Report and Written Opinion dated Jan. 18, 2022 from counterpart International Patent Application No. PCT/IB2021/058650.
Rozzi Giacomo et al: "Conclusions", Interactive Cardiovascular and Thoracic Surgery, vol. 29, No. 4, Jun. 9, 2019, pp. 625-631, XP055773422, DOI: 10.1093/icvts/ivz120 Retrieved from the Internet: URL:http://academic.oup.com/icvts/articlepdf/29/4/625/30053366/ivz120.pdf [retrieved on Feb. 8, 2021].
Uematsu M et al: "Development of "Patient Robot"; Measurement System of Myocardial Behaviors for the Quantitative Evaluation of the Surgical Robot Technology", Biomedical Robotics and Biomechatronics, 2006. BIOROB 2006. The First IEEE/RAS-EMBS International Conference on Pisa, Italy Feb. 20-22, 2006, Piscataway, NJ, USA, IEEE, Piscataway, NJ, USA, Feb. 20, 2006, pp. 655-660, XP010922584, DOI: 10.1109/BIOROB.2006.1639164 ISBN: 978-1-4244-0040-9.
Watanabe et al: "Three-dimensional quantification of cardiac surface motion: A newly developed three-dimensional digital motion-capture and reconstruction system for beating heart surgery", The Journal of Thoracic and Cardiovascular Surgery, Mosby-Year Book, Inc., St. Louis, MO, US, vol. 132, No. 5, Nov. 1, 2006, pp. 1162-1171, XP005711889, ISSN: 0022-5223, DOI: 10.1016/J.JTCVS.2006.07.017.
Lorenzo Fassina et al: "Cardiac kinematic parameters computed from video of in situ beating heart", arxiv.org, Cornell University Library, 201 Olin Library Cornell University Ithaca, NY 14853, Feb. 5, 2020, P081592937, DOI: 10.1038/SREP46143.
Lo Muzio Francesco Paolo et al: "In-situ optical assessment of rat epicardial kinematic parameters reveals frequency-dependent mechanic heterogeneity related to gender", Progress in Biophysics and Molecular Biology, Elsevier, Amsterdam, NL, vol. 154, May 21, 2019, pp. 94-101, XP086193859, ISSN: 0079-6107, DOI: 10.1016/J.PBIOMOLBIO.2019.05.003 [retrieved on May 21, 2019].
Bogatyrenko E. et al: "Simultaneous state and parameter estimation for physics-based tracking of heart surface motion", Multisensor Fusion and Integration for Intelligent Systems (MFI), 2010 IEEE Conference on, IEEE, Piscataway, NJ, USA, Sep. 5, 2010, pp. 109-114, XP031777441, ISBN: 978-1-4244-5424-2.
Bogatyrenko E. et al: "Efficient physics-based tracking of heart surface motion for beating heart surgery robotic systems", International Journal of Computer Assisted Radiology and Surgery, vol. 6, No. 3, Aug. 6, 2010, pp. 387-399, XP055202161, ISSN: 1861-6410, DOI: 10.1007/s11548-010-0517-5.
Hayashibe et al: "Robotic surgery setup simulation with the integration of inverse-kinematics computation and medical imaging", Computer Methods and Programs in Biomedicine, Elsevier, Amsterdam, NL, vol. 83, No. 1, Jul. 1, 2006 , pp. 63-72, XP005543789, ISSN: 0169-2607.
Japanese Office Action dated Jun. 25, 2025 from counterpart Japanese App No. 2023516811.

* cited by examiner

APPARATUS FOR THE DETECTION OF AT LEAST ONE PARAMETER, IN PARTICULAR KINETIC, IN RELATION TO THE HEART, OR THE MYOCARDIUM, OF A HUMAN BEING OR AN ANIMAL

This application is the National Phase of International Application PCT/IB2021/058650 filed Sep. 22, 2021 which designated the U.S.

This application claims priority to Italian Patent Application No. 102020000022480 filed Sep. 23, 2020, which applications are incorporated by reference herein.

FIELD OF APPLICATION OF THIS INVENTION

The present invention refers to an apparatus for the detection of at least one parameter, in particular kinetic, in relation to the heart, or myocardium, of a human being or an animal.

In particular, the apparatus can be used during surgical operations, in particular performed on the heart, or myocardium itself, inside a corresponding operating theatre.

BACKGROUND

An apparatus for the detection of at least one parameter, in particular kinetic, in relation to the heart, or myocardium, of a human being or an animal, especially for use during surgical operations, in particular performed on the heart, or myocardium itself, inside a corresponding operating theatre, is known.

Said already known apparatus comprises a detection means for the detection of spatial or mechanical, movements of said heart, or myocardium, and a control means, or processor of the apparatus, in particular adapted to, or configured to, process the signals, or data, provided by said detection means for providing at least one corresponding parameter, in particular kinetic, in relation to said heart, or myocardium, of said human being or animal.

This already known apparatus uses a 2D television camera for the detection of the patient's heart, but this has many limitations and does not allow a good kinetics of the patient's heart to be obtained, which cannot therefore be conveniently assessed by the clinician.

In addition, due to the fact that there are very bright lights in the operating theatre that the surgeon needs in order to have a good view at all times during the operation, however, light refractions occur that can lead to problems in processing the 2D images detected, with the risk of obtaining totally misleading data.

Moreover, said already known apparatus is manually positioned, with difficulty and discomfort on the part of the operator, at the patient's heart, in the pre-operating step, then removed and repositioned, again at the same heart of the patient, in the post-operating step, which leads, for obvious reasons, to positions that will never be perfectly coincident with each other and which consequently lead to clinical comparisons that are invalidated by such a technical distortion.

In particular, according to the prior art, it is not possible to obtain a particularly accurate detection of the kinetics of the heart, and in particular it is not possible to assess the ejection fraction, the fractional shortening and the ventricular hemodynamic load of said heart, or myocardium, without resorting to particularly invasive techniques for the patient.

SUMMARY OF THE INVENTION

With the present invention it is therefore wished to propose a new solution and an alternative to the solutions known up to now and in particular it is proposed to overcome one or more of the drawbacks or problems referred to above, and/or to satisfy one or more requirements referred to above and/or in any case experienced in the art, and in particular which can be deduced from the above.

An apparatus is therefore provided for the detection of at least one parameter, in particular kinetic, in relation to the heart, or the myocardium, of a human being or an animal, especially the apparatus being usable during surgical operations, in particular performed on the heart, or myocardium, itself, inside a corresponding operating theatre; comprising a detection means for the detection of spatial or mechanical, movements of said heart, or myocardium, and a control means, or processor, of the apparatus, in particular adapted to, or configured to, process the signals, or data, provided by said detection means for providing at least one corresponding parameter, in particular kinetic, in relation to said heart, or myocardium, of a human being or animal; characterized in that said detection means for the detection of the spatial, or mechanical, movements of said heart, or myocardium, is adapted to detect the distance, or depth, i.e. the variation in distance, or depth, of one or more points of said heart, or myocardium, in particular of one or more points of a corresponding surface or wall of said same heart, or myocardium, by the detection means for detecting the spatial, or mechanical, movements of said heart, or myocardium.

In this way, a particularly accurate detection of the kinetics of the heart is obtained, in particular it is possible to assess the ejection fraction, the fractional shortening and the ventricular hemodynamic load of said heart, or myocardium, all with an apparatus that is in itself non-invasive for the patient.

BRIEF DESCRIPTION OF THE DRAWINGS

This and other innovative aspects or respective advantageous embodiments, are however, set forth in the appended claims, the technical characteristics of which can be found, together with corresponding advantages achieved, in the following detailed description, illustrating a purely non-limiting example of the embodiment of the invention, which is made with reference to the appended drawings, in which:

DETAILED DESCRIPTION OF PREFERRED EMBODIMENTS OF THE INVENTION

Figure 1B:
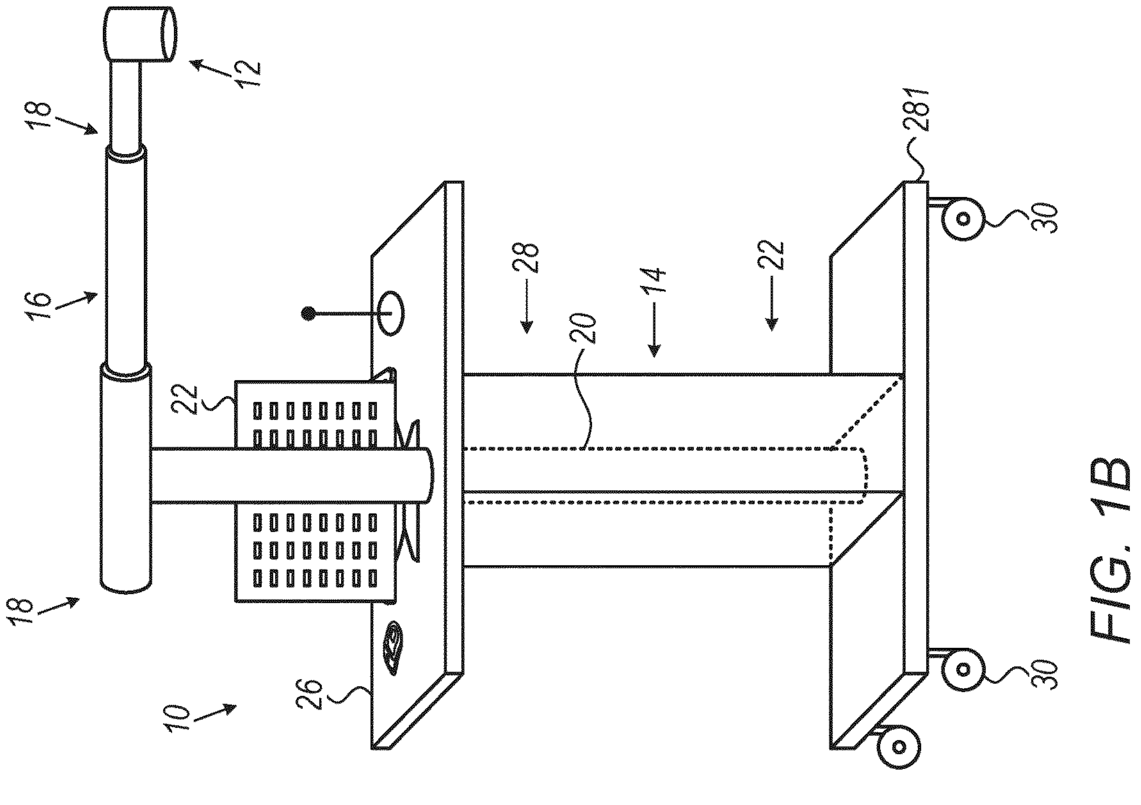
FIG. 1B illustrates a schematic rear perspective view of the preferred embodiment of the apparatus according to the present invention.

A preferred embodiment 10 of apparatus for the detection of at least one parameter, in particular kinetic, in relation to the heart, or the myocardium, 11 of a human 13 or an animal is illustrated in the attached figures.

In particular, the apparatus 10 can be used during surgical operations, in particular performed on the heart, or myocardium 11 itself, inside a corresponding operating theatre 15.

Figure 1A:
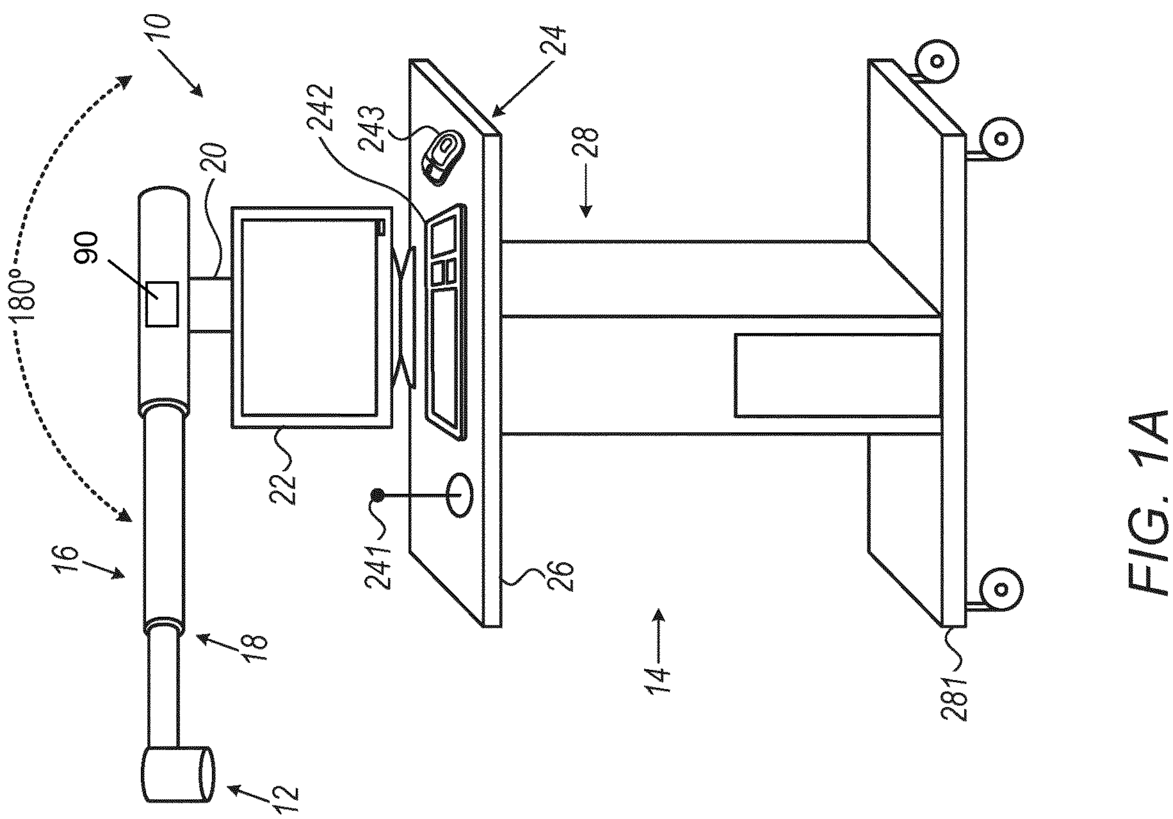
FIG. 1A illustrates a schematic front perspective view of a preferred embodiment of the apparatus according to the present invention.
Figure 2:
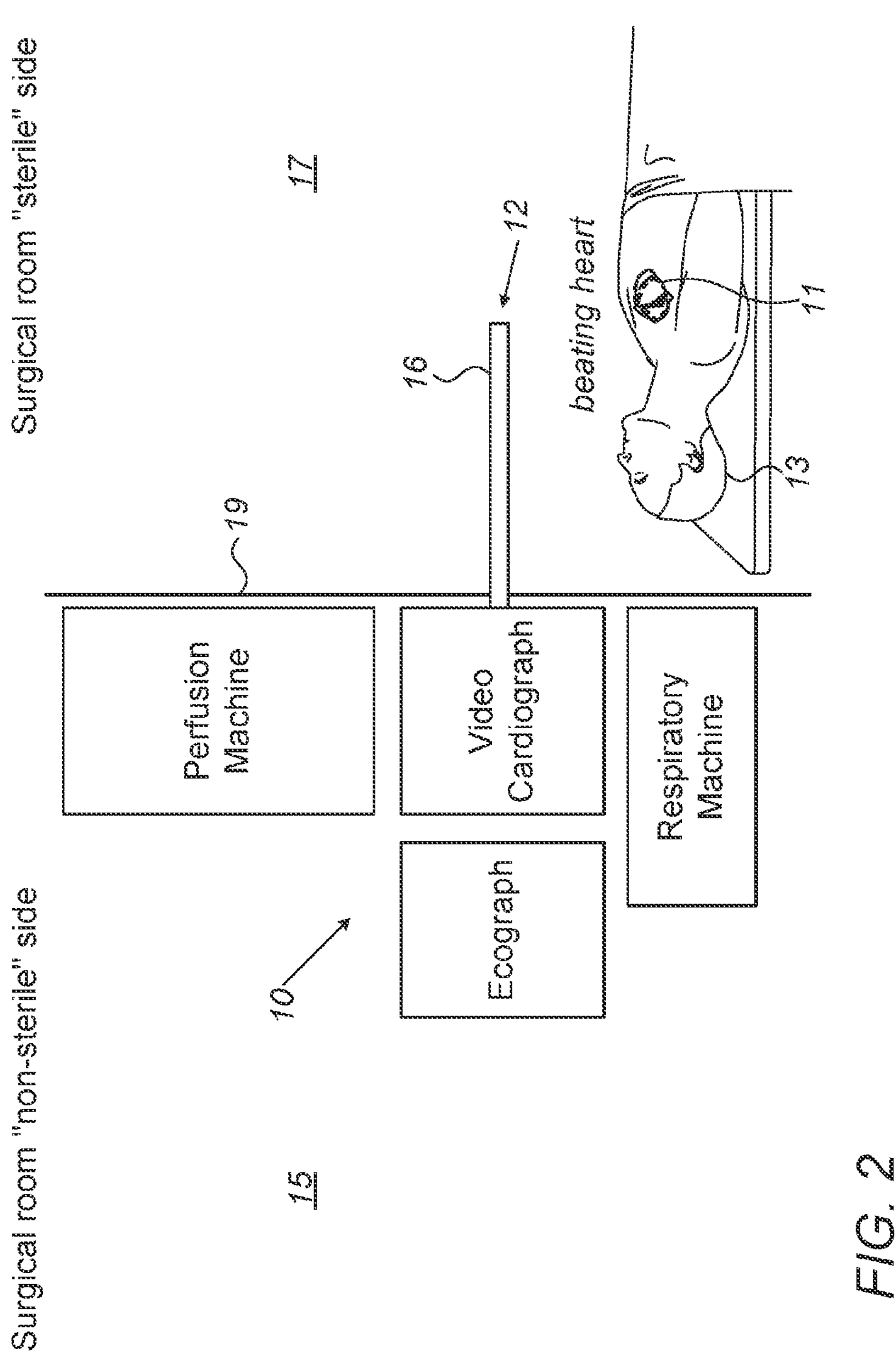
FIG. 2 illustrates a schematic view of the operating theatre configured for an advantageous use of the preferred embodiment of apparatus according to the present invention.

As is particularly clear from FIGS. 1A, 1B and 2, the apparatus 10 comprises a detection means 12 for the detection of spatial or mechanical, movements of said heart, or myocardium, 11, and a control means, or processor, 14 of the apparatus, in particular adapted to, or configured to, process the signals, or data, provided by said detection means 12 for providing at least one corresponding parameter, in particular kinetic, in relation to said heart, or myocardium, 11 of a human being 13 or animal.

Advantageously, said detection means 12 for the detection of the spatial, or mechanical, movements of said heart, or myocardium, 11 is adapted to detect the distance, or depth, z, i.e. the variation in distance, or depth, of one or more points of said heart, or myocardium, 11, in particular of one or more points of a corresponding surface or wall of the same heart, or myocardium, 11, by said detection means 12 for detecting the spatial, or mechanical, movements of said heart, or myocardium 11.

In this way, a particularly accurate detection of the kinetics of the heart is obtained, in particular it is possible to assess the ejection fraction, the fractional shortening and the ventricular hemodynamic load of said heart, or myocardium, 11, all with an apparatus that is in itself non-invasive for the patient.

In particular, the distance, or depth, z from said heart, or myocardium, 11, or from the respective surface or wall thereof, means the distance of the objective of the same television camera from said heart, or myocardium, 11, i.e. from the respective surface or wall thereof.

Advantageously, said detection means of said heart, or myocardium, 11, is adapted to detect the movement, or displacement, of one or more points of said heart, or myocardium, 11, i.e. one or more points of said heart, or myocardium, 11, in a corresponding plane, i.e. with respect to corresponding Cartesian reference axes x, y in said plane, particularly perpendicular to the detection direction of said depth z by the detection means 12 for detecting the spatial or mechanical, movements, of said heart, or myocardium, 11.

Advantageously, said detection means 12 for the detection of the spatial, or mechanical, movements of said heart, or myocardium, 11 comprises, or is in the form of, a corresponding television camera.

With advantage, said detection means 12 for detecting the spatial, or mechanical movements, of said heart, or myocardium, 11, comprises, or is in the form of, a 3D television camera, in particular adapted to detect images of said heart, or myocardium, 11, i.e. of a corresponding surface of wall of said same heart, or myocardium, 11, in a corresponding plane x, y, with detection of the perpendicular depth z of the same points of the image according to said plane x, y.

Advantageously, as can be seen from said figures, said detection means 12 for detecting the spatial, or mechanical, movements of said heart, or myocardium, 11, or television camera, 12, i.e. in particular the respective objective thereof, is placed at a distance from said heart, or myocardium, 11, i.e. from the respective surface or wall thereof, which is comprised between 10 cm and 80 cm, preferably between 30 cm and 50 cm.

With advantage, as can be seen from said figures, said detection means 12 for the detection of the spatial, or mechanical, movements of said heart, or myocardium, 11, detects the same heart, or myocardium, 11 for a time interval comprised between 1 second and 30 seconds, preferably around 15-20 seconds.

As can be seen from said figures, advantageously, support means, or station, 16 of said detection means 12 for the detection of the spatial, or mechanical, movements of said heart, or myocardium, 11, is provided.

With particular advantage, said support means 16 of said detection means, or television camera, 12 for detecting the spatial, or mechanical movements, of said heart, or myocardium, 11, is adapted to move, or displace, the same detection means 12 for detecting the spatial, or mechanical movements, of said heart, or myocardium, 11 with respect to said heart, or myocardium, 11, or to a corresponding surface, or wall, of the same heart, or myocardium, 11.

With particular advantage, said detection means 16, or television camera, 12 for detecting the spatial, or mechanical movements, of said heart, or myocardium, 11, is adapted to move said detection means, or television camera, 12 for detecting the spatial, or mechanical movements, of said heart, or myocardium, 11 perpendicularly with respect to said heart, or myocardium, 11, or to the corresponding surface, or wall, thereof.

As can be seen from said figures, advantageously, said support means 16 of said detection means, or television camera, 12 for detecting the spatial, or mechanical movements, of said heart, or myocardium, 11, is adapted to move said detection means, or television camera, 12 for detecting the spatial, or mechanical movements, of said heart, or myocardium, 11, in a corresponding plane parallel to said heart, or myocardium, 11, i.e. to the corresponding surface or wall thereof, in particular to the support plane of said patient 13, or to the floor of said operating theatre 15.

Advantageously, as can be seen from said figures, said support means 16 of said detection means, or television camera, 12 for detecting the spatial, or mechanical movements, of said heart, or myocardium, 11, is adapted to position said means, or television camera, 12 of the spatial, or mechanical movements, of said heart, or myocardium, 11 above and distanced from the same heart, or myocardium, 11, in particular perpendicularly aligned with said heart, or myocardium, 11.

Particularly advantageously, as can be seen from said figures, said control means, or processor, 14 of the apparatus is configured to position said detection means, or television camera, 12 for detecting the spatial, or mechanical movements, of said heart, or myocardium, 11, in a corresponding and predetermined position with respect to said heart, or myocardium, 11, or with respect to a corresponding surface, or wall thereof.

As can be seen from said figures, in a particularly advantageous way, said control means, or processor, 14 of the apparatus is configured to store the position of said detection means, or television camera, 12 for detecting the spatial, or mechanical movements, of said heart, or myocardium, 11, in a predetermined position with respect to said heart, or myocardium, 11, or to a corresponding surface, or wall thereof, and to reposition, in particular selectively or automatically, said detection means, or television camera, 12 for detecting the spatial, or mechanical, movements of said heart, or myocardium, 11 in said stored position.

Advantageously, as can be seen from said figures, in particular in the apparatus 10, a detector 90 is provided for detecting the position of said support means 16 of said detection means, or television camera, 12 for detecting the spatial, or mechanical movements, of said heart, or myocardium, 11, which is in communication with said control means, or processor, 14 of the apparatus for determining the position of said detection means or television camera, 12 of the spatial, or mechanical movements, of said heart, or myocardium, 11.

Figure 3:
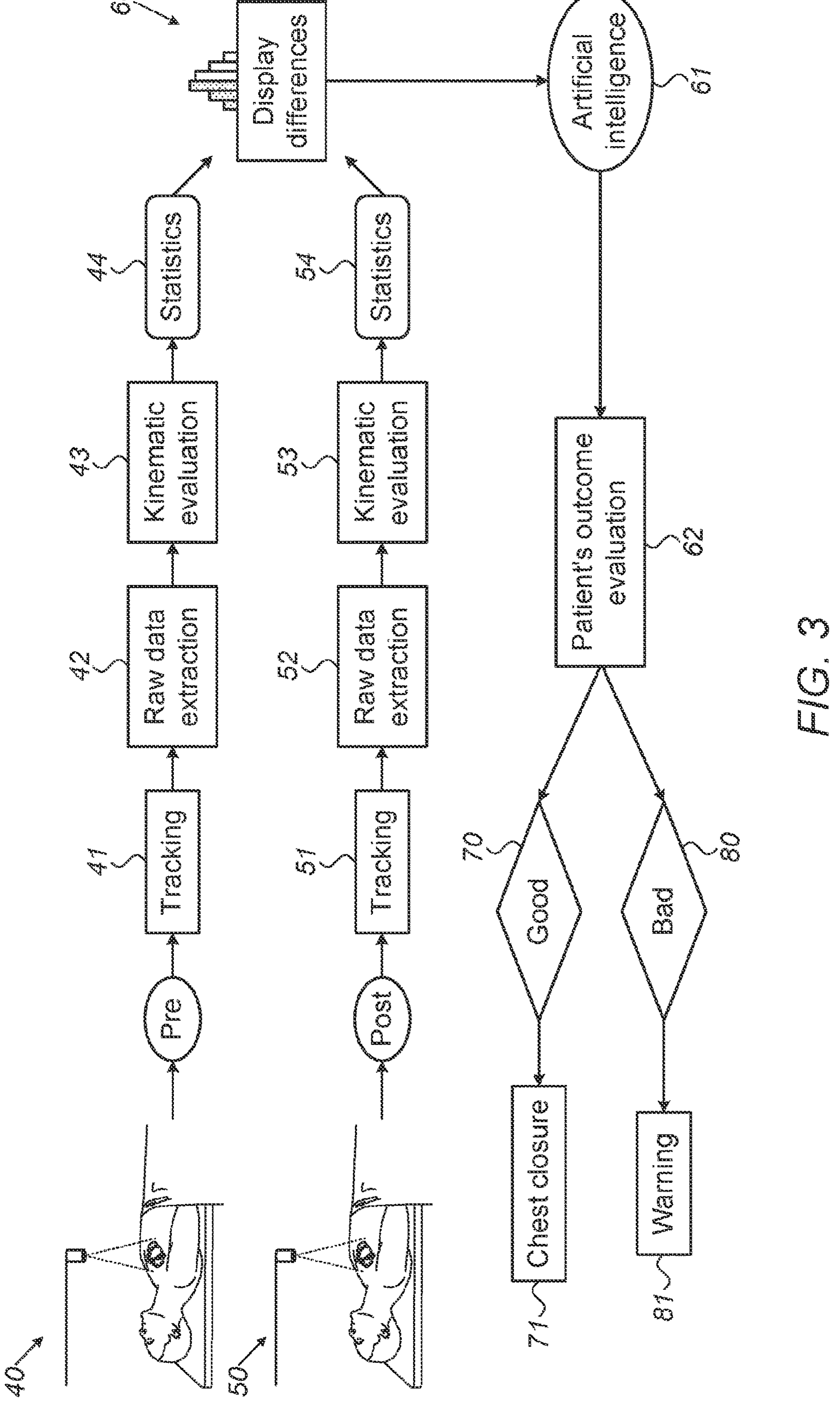
FIG. 3 illustrates a flow diagram of the operation of the preferred embodiment of apparatus according to the present invention.

Advantageously, as can be seen from said figures, said detection means, or television camera, 12 for detecting the spatial, or mechanical, movements, of said heart, or myocardium, 11, is adapted to detect said heart, or myocardium, 11 in a first and in a second operating condition, i.e. in particular in a pre-operating step 40 and in a post-operating step 50, as can be clearly seen from the following FIG. 3. According to a further embodiment, however, it would also be conceivable for a detection to take place in an intra-operating step.

As can be seen from said figures, advantageously, said control means, or processor, 14 of the apparatus is configured to determine, starting from corresponding signals, or data, received from said detection means, or television camera, 12 for detecting the spatial, or mechanical, movements, of said heart, or myocardium, 11, one or more of the following parameters, in particular kinetic, of the heart, or myocardium, 11 of a human being 13 or animal: force of contraction, cardiac fatigue, kinetic energy of contraction, contraction speed, punctiform displacement of the trajectory, area and perimeter of the trajectory, analysis of the systole and diastole times of the individual beat.

Advantageously, as can be seen from said figures, said control means, or processor, 14 of the apparatus is configured to determine, starting from corresponding signals, or data, received from said detection means, or television camera, 12 for detecting the spatial, or mechanical, movements, of said heart, or myocardium, 11, evaluate one or more of the following parameters, in particular kinetic, of the heart, or myocardium, 11 of a human being 13 or animal: the ejection fraction, the fractional shortening, the ventricular hemodynamic load of said heart, or myocardium, 11.

With advantage, as can be seen from said figures, said support means 16 of said detection means, or television camera, 12 for detecting the spatial, or mechanical movements, of said heart, or myocardium, 11, comprises an elongated support arm 18, in particular at the respective free end, of said detection means, or television camera, 12 for detecting the spatial, or mechanical, movements, of said heart, or myocardium, 11.

As can be seen from said figures, advantageously, said elongated support arm 18 of said means, or television camera, 12 for detecting the spatial, or mechanical, movements, of said heart, or myocardium, 11, extends, in particular backwards, from said apparatus 10, especially, during use, towards the patient and/or beyond a separation 19 between the sterile area of the operating theatre 15 and the non-sterile area, for housing technical equipment to assist with the operation 17. In particular, said separation is defined by the drape 19, which prevents pollution of the operating field, with said arm 16 that extends above the support or underwire from which said drape 19 is hung.

Advantageously, as can be seen from said figures, said elongated support arm 18 of said means, or television camera, 12 for detecting the spatial, or mechanical, movements, of said heart, or myocardium, 11, is axially extensible, or telescopic.

With particular advantage, as can be seen from said figures, said elongated support arm 18 of said detection means, or television camera, 12 for detecting the spatial, or mechanical, movements, of said heart, or myocardium, 11, is rotatable, in particular with respect to a corresponding perpendicular, or vertical, axis according to opposite angular directions, especially for an angular portion around 180°.

As can be seen from said figures, advantageously, said elongated support arm 18 of said detection means, or television camera, 12 for detecting the spatial, or mechanical, movements, of said heart, or myocardium, 11, can be perpendicularly or vertically raised and lowered, in particular with respect to said heart, or myocardium, 11.

Advantageously, as can be seen from said figures, said support means 16 of said detection means, or television camera, 12 for detecting the spatial, or mechanical, movements, of said heart, or myocardium, 11, comprises an upright 20 that supports said elongated support arm 18 of said detection means, or television camera 12 and from which the same extends, for detecting the spatial, or mechanical, movements, of said heart, or myocardium, 11.

In a particularly advantageous manner, as can be seen from said figures, said upright 20 for supporting said elongated support arm 18 of said detection means, or television camera, 12 for detecting the spatial, or mechanical, movements, of said heart, or myocardium, 11, extends perpendicularly or vertically.

As can be seen from said figures, advantageously, said support upright 20 of said elongated support arm 18 of said detection means, or television camera, 12 for detecting the spatial, or mechanical, movements, of said heart, or myocardium, 11, is axially extensible, i.e. it can be raised and lowered, in particular for raising and lowering said elongated support arm 18 of said detection means, or television camera, 12 for detecting the spatial, or mechanical, movements, of said heart, or myocardium, 11.

Advantageously, as can be seen from said figures, said apparatus 10 comprises a display screen 22 in particular supported on a corresponding support surface 26 of the apparatus 10.

Advantageously, as can be seen from said figures, said apparatus 10 comprises an input means 24, especially said control means, or processor, 14 of the apparatus, in particular comprising a joystick 241 for controlling said support arm 18 and/or a keyboard 242 and/or a trackpad or mouse 243, in particular supported on a corresponding support surface 26 of said apparatus 10, or also integrated in the structure of the station.

As can be seen from said figures, advantageously, said apparatus 10 comprises a support structure 28, in particular of said support means 16 of said detection means, or television camera, 12 for detecting the spatial, or mechanical, movements, of said heart, or myocardium, 11 and/or of said support surface 26 of the apparatus 10.

Advantageously, as can be seen from said figures, said support structure 28 comprises a lower base 281 in particular on which said control means, o processor, 14 of the apparatus is supported and/or from which a corresponding column 282 extends, in particular for supporting said support surface 26 of the apparatus 10.

With advantage, as can be seen from said figures, on said support structure 28, said control means, or processor, 14 of the apparatus is positioned in front of said support upright 20 of said elongated support arm 18 of said detection means, or television camera, 12 for detecting the spatial, or mechanical, movements, of said heart, or myocardium, 11.

As can be seen from said figures, advantageously, said support upright 20 of said elongated support arm 18 of said detection means, or television camera, 12 for detecting the spatial, or mechanical, movements, of said heart, or myocardium, 11, is provided in the rear area of said support structure 28 and backwards.

Advantageously, as can be seen from said figures, said support structure 28 comprises a roller means, in particular swivelling, 30, in particular fixed to said lower base 281 of said support structure 28, and preferably comprising, as illustrated in FIGS. 1A and 1 B, rollers for ground support, and being provided with a locking means of the movement of said apparatus 10, i.e. for locking the rotation of said roller means, in particular of the swivelling type, 30.

With particular advantage, as can be seen from said figures, said control means, or processor, 14 of the apparatus is configured to position perpendicularly, or vertically, said detection means or television camera, 12 for detecting the spatial, or mechanical, movements, of said heart, or myocardium, 11, in particular as a function of corresponding signals, or data, received from said detection means 12 of the distance, or depth, z, of said heart, or myocardium, 11, i.e. using the depth parameter of said 3D television camera.

As can be seen from said figures, advantageously, said control means, or processor, 14 of the apparatus is configured to define the means for the positioning in perpendicular, or vertical, alignment of said detection means, or television camera, 12 for detecting the spatial, or mechanical, movements, of said heart, or myocardium, 11, of the patient, and in particular defined by an image in transparency of said heart, or myocardium, 11, to collimate by the operator manoeuvring said elongated support arm 18 of said detection means, or television camera, 12 for detecting the spatial, or mechanical, movements, of said heart, or myocardium, 11, i.e. automatically, and that is preferably displayed on said display screen of the apparatus 10.

As can be seen from said FIG. 3, advantageously, said control means, or processor, 14 of the apparatus is configured, or has corresponding software, for performing, in particular in both of said steps, preferably in said pre-operative step 40 and/or in said post-operative step 50, particularly in sequence and preferably automatically, a tracking step, 41, 51 of the spatial, or mechanical, movements, of said heart, or myocardium, 11, or of corresponding points thereof to be tracked, an extraction step 42, 52 of the coordinates x, y, z of said tracked movement, in 41, 51, of said heart, or myocardium, 11, and an evaluation or calculation step 43, 53 of said one or more parameters, in particular kinetic, in relation to said heart, or myocardium, 11, in particular starting from said coordinates x, y, z extracted from said tracked movement in 41, 51 of said heart, or myocardium, 11, as well as a possible implementation 44, 54 of a statistic, in particular weighted according to the number of recordings or detections performed, for said one or more parameters, in particular kinetic, evaluated, or calculated, in relation to said heart, or myocardium, 11.

Advantageously, as can be seen from said figures, moreover, said control means, or processor, 14 of the apparatus is configured, or has corresponding software, to display, in particular once said post-operative verification procedure 50 has been performed, in particular in sequence therewith and preferably automatically following it 60, in particular on said display 22 of the apparatus 10, the differences between said one or more parameters, in particular kinetic, evaluated, or calculated, in relation to said heart, or myocardium, 11 in said first and second step, i.e. in said pre-operative 40 and post-operative steps 50.

In this way, the clinician can advantageously evaluate the success of the intervention.

As can be seen from said figures, advantageously, said control means, or processor, 14 of the apparatus is configured, or has corresponding software, to perform, in particular following said post-operative step 50, and especially in sequence with said display step 60, preferably automatically, an artificial intelligence procedure for the recognition of the state of said heart, or myocardium, 11, and to obtain corresponding results or outcomes, respectively positive 70 or negative 80 and, following the respective outcome, to control the emission of a corresponding signal 71, e.g. of the visual type, and preferably shown on said display 22, for consent for the continuation of the operation, i.e. consent to close the patient's chest, or to control the emission of a warning signal 81 of the presence of a problem for said patient.

In practice, as is evident, the technical characteristics illustrated above allow, individually or in a respective combination, achieving one or more of the following advantageous results:

- a particularly accurate detection of the kinetics of the heart is obtained, in particular it is possible to evaluate the ejection fraction, the fractional shortening, the ventricular hemodynamic load of said heart, or myocardium, all with an apparatus which is in itself non-invasive for the patient, as well as the force of contraction, cardiac fatigue, kinetic energy of contraction, contraction speed, punctiform displacement of the trajectory, area and perimeter of the trajectory, analysis of the systole and diastole times of the individual beat;
- the clinician can advantageously evaluate the success of the operation.

The present invention is susceptible to evident industrial application. The person skilled in the art will also be able to imagine numerous modifications and/or variations to be made to the same invention, while remaining within the scope of the inventive concept, as extensively explained. Moreover, the person skilled in the art will be able to imagine further preferred embodiments of the invention which include one or more of the above illustrated characteristics of the preferred embodiment. Moreover, it must also be understood that all the details of the invention can be replaced by technically equivalent elements.

The invention claimed is:

1. An apparatus for detection of at least one kinetic parameter in relation to a heart or myocardium of a human being or an animal, the apparatus being usable during surgical operations performed on the heart or myocardium, inside a corresponding operating theatre; the apparatus comprising

- a detection device configured for detection of spatial or mechanical, movements of said heart or myocardium;
- a control processor adapted to process signals or data provided by said detection device for providing at least one corresponding kinetic parameter in relation to said heart or myocardium;
- wherein said detection device is adapted to detect a distance or depth, or a variation in the distance or depth of one or more points of a corresponding surface or wall of said heart or myocardium;
- wherein said detection device is adapted to detect a movement or displacement of one or more points of said heart or myocardium in a corresponding plane with respect to corresponding Cartesian reference axes (x, y) in said plane, perpendicular to a detection direction of said distance or depth by the detection device;
- a support device configured for supporting said detection device, the support device comprising an elongated support arm at a respective free end of said detection device;
- wherein said detection device is a 3D television camera adapted to detect images of the corresponding surface or wall in the corresponding plane with detection of a perpendicular depth (z) of the one or more points according to said plane (x, y);
- wherein said elongated support arm is movable perpendicularly or vertically raised and lowered, with respect to said heart or myocardium; and
- wherein said control processor is configured to position perpendicularly, or vertically, said detection device as a function of the signals or data provided by said detection device of the distance or depth of said heart or myocardium using the depth detected by said 3D television camera.

2. The apparatus according to claim 1, wherein an objective of said detection device is configured to be positioned at a distance between 30 cm and 50 cm from the corresponding surface or wall.

3. The apparatus according to claim 1, wherein said support device is adapted to move the detection device with respect to said heart or myocardium or to the corresponding surface or wall.

4. The apparatus according to claim 3, wherein said support device is adapted to move said detection device perpendicularly with respect to said heart or myocardium or to the corresponding surface or wall.

5. The apparatus according to claim 3, wherein said support device is adapted to move said detection device in a corresponding plane parallel to a support plane of said patient, or to a floor of said operating theatre.

6. The apparatus according to claim 1, wherein said support device is adapted to position said detection device above and distanced from the heart or myocardium and perpendicularly aligned with the heart or myocardium.

7. The apparatus according to claim 1, wherein said control processor is configured to store a position of said detection device in a predetermined position with respect to said heart or myocardium or to the corresponding surface or wall, and to reposition, selectively or automatically, said detection device in said stored position.

8. The apparatus according to claim 1, and further comprising a detector configured for detecting a position of said support device, the detector being in communication with said control processor.

9. The apparatus according to claim 1, wherein said detection device is adapted to detect said heart or myocardium in a first and in a second operating condition.

10. The apparatus according to claim 1, wherein said control processor is configured to determine, starting from the signals or data provided by said detection device, one or more of the following parameters of the heart or myocardium: force of contraction, cardiac fatigue, kinetic energy of contraction, contraction speed, punctiform displacement of a trajectory, area and perimeter of the trajectory, analysis of systole and diastole times of an individual beat; and/or said control processor is configured to evaluate, starting from the signals or data provided by said detection device, one or more of the following parameters of the heart or myocardium: an ejection fraction, a fractional shortening, and a ventricular hemodynamic load.

11. The apparatus according to claim 1, wherein said elongated support arm is axially extensible, or telescopic.

12. The apparatus according to claim 1, wherein said elongated support arm is rotatable with respect to a corresponding perpendicular, or vertical, axis according to opposite angular directions.

13. The apparatus according to claim 1, wherein said support device comprises a support upright that supports said elongated support arm, the support upright being extendable perpendicularly or vertically; and wherein said support upright is also axially extensible, for raising and lowering said elongated support arm.

14. The apparatus according to claim 1, and further comprising a support structure configured for supporting said support device and/or a support surface of the apparatus.

15. The apparatus according to claim 14, wherein said support structure comprises a lower base on which said control processor is supported and/or from which a corresponding column extends for supporting said support surface.

* * * * *